(12) United States Patent
Hunter

(10) Patent No.: US 6,371,453 B1
(45) Date of Patent: Apr. 16, 2002

(54) DIFFUSER FOR MOUNTING A VOLATILIZABLE SUBSTANCE ABOVE A CONTAINER OF HEATED LIQUID

(75) Inventor: Neil Edwin Hunter, Farnham (GB)

(73) Assignee: Earlex Limited, Guildford (GB)

(*) Notice: Subject to any disclaimer, the term of this patent is extended or adjusted under 35 U.S.C. 154(b) by 0 days.

(21) Appl. No.: 09/491,665

(22) Filed: Jan. 27, 2000

(30) Foreign Application Priority Data

Jan. 29, 1999 (GB) .............................. 9901890

(51) Int. Cl.$^7$ ................ B01F 3/04; A61L 9/04
(52) U.S. Cl. ............... 261/107; 261/142; 261/DIG. 88; 261/DIG. 89; 422/125; 239/56
(58) Field of Search ............... 261/107, 142, 261/DIG. 88, DIG. 89; 422/123, 125; 239/55, 56, 57

(56) References Cited

U.S. PATENT DOCUMENTS

| 571,811 A | * | 11/1896 | Valentine | 422/125 |
| 843,705 A | * | 12/1907 | Seligsohn | 422/125 |
| 1,202,485 A | * | 10/1916 | Cohn | 422/125 |
| 2,515,310 A | * | 7/1950 | Messina, Jr. | 422/125 |
| 4,595,564 A | * | 6/1986 | Spector et al. | 422/125 |
| 5,904,028 A | * | 5/1999 | Fujiura et al. | 239/56 |

* cited by examiner

Primary Examiner—Robert A. Hopkins
(74) Attorney, Agent, or Firm—Ware, Fressola, Van Der Sluys & Adolphson LLP

(57) ABSTRACT

A diffuser 1 for diffusing essential oil into a room using steam comprising a housing 2, a liquid container 6 in the housing, a heater 11 for heating the liquids in the container 6 to vaporize it, and a support 5 for holding volatilizable-substance matter 20 above the liquid container. For convenience, the volatilizable-substance matter 20 is in the form of an aroma packet, having upper 22 and lower 23 cellulose tissue webs, holding between them some dried plant material, for example lavender blooms. The webs are sealed together at their edges by a rim, which is sized to fit the support of the diffuser.

14 Claims, 1 Drawing Sheet

DIFFUSER FOR MOUNTING A VOLATILIZABLE SUBSTANCE ABOVE A CONTAINER OF HEATED LIQUID

TECHNICAL FIELD

The present invention relates to a diffuser for diffusing volatile substances by application of water vapour.

BACKGROUND OF THE INVENTION

It is known to bubble steam through an essential oil for diffusing the oil into the atmosphere of the room containing the diffuser.

Many volatile substances are contained in dried organic/plant/vegetable matter and gums & resins; and can be released by passing water vapour over the matter.

The object of the invention is to provide a diffuser for diffusing such volatile substances.

SUMMARY OF THE INVENTION

According to the invention there is provided a diffuser comprising:

a housing;

a liquid container in the housing;

a heater for the liquid container, adapted to heat the container sufficiently to vaporise liquid in the container; and a support for holding volatilisable-substance matter above the liquid container.

Whilst it can be envisaged particularly for automotive use that the liquid container be substantially closed—with of course a water vapour outlet—normally the liquid container will be open within the housing.

Also, although it can be envisaged that the support could be integral with the liquid container, it is preferably provided on an extension of the housing above the container.

A perforate member, such as a grid or grill, could be provided for the volatilisable-substance matter. This will normally be provided as the original organic/plant/vegetable form, albeit dried. In an alternative,. it may be provided in the form of an extract such as an essential oil. For volatilisation, the extract may be applied to an absorbent pad—such as of foam or felt material—supported on the grid, or into a smaller container—such as a dish—again supported on the grid. However, the volatilisable-substance matter is preferably provided in a disposable packet, itself supportable directly on the support.

Normally a perforate cover will be provided over the support.

According to another aspect of the invention there is provided a disposable packet of volatilisable-substance matter for use with the diffuser of the invention, the packet comprising:

a porous envelope, which is at once sufficiently porous to allow passage of steam and sufficiently strong to retain its integrity in steam, a rim adapted to fit the diffuser's support and a quantity of volatilisable-substance matter enclosed within the porous envelope.

In the preferred embodiment, the envelope comprises an upper web and a lower web, each of tissue and each attached to the rim. Preferably, the webs and the rim are of cellulose material.

BRIEF DESCRIPTION OF THE DRAWINGS

To help understanding of the invention, a specific embodiment thereof will now be described with reference to the accompanying drawing, in which.

BEST MODE FOR CARRYING OUT THE INVENTION

Figure 1:
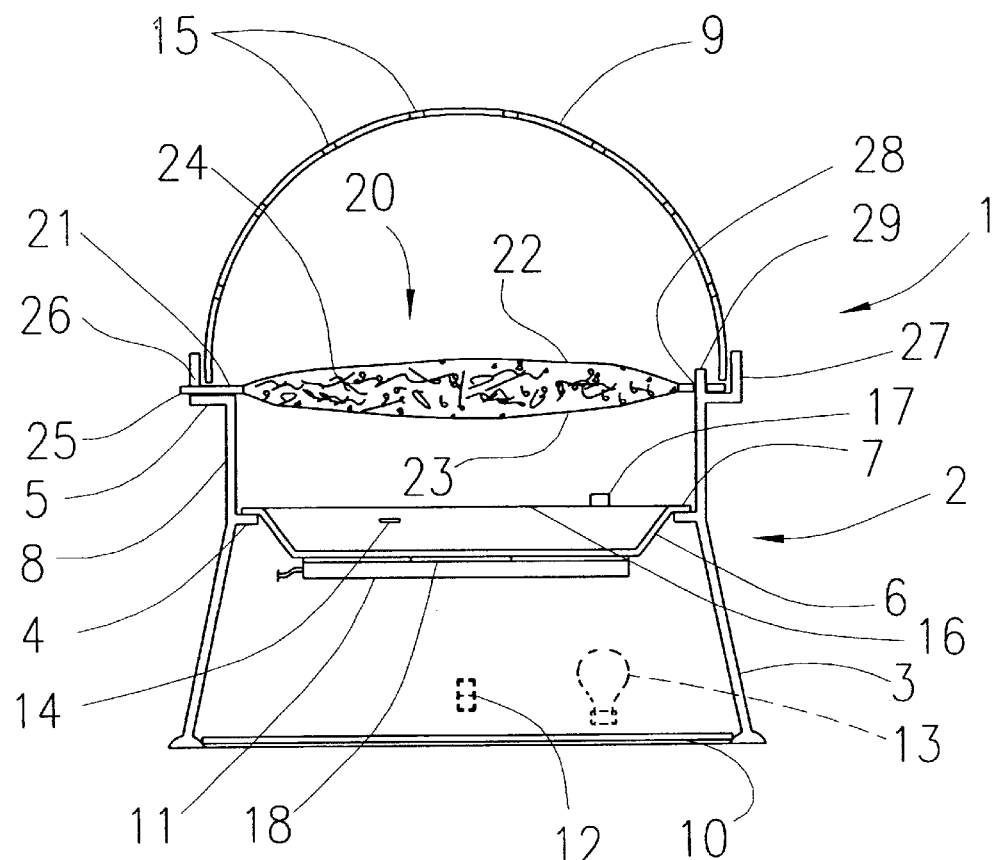
FIG. 1 is a cross-sectional side view of diffuser of the invention, with a packet of volatilisable-substance matter in position

The diffuser 1 has a housing 2 of moulded plastics material and based on a shell moulding 3. This has two internal ledges 4,5. To the lower, smaller diameter ledge 4, a stainless steel or treated alloy bowl 6 is attached at a rim 7 of the bowl by interference fit or odourless adhesive. An extension 8 of the shell has the other ledge 5 at its top. A perforate moulded dome rests 9 on the upper ledge 5. A moulded base 10 closes the bottom of the shell.

Attached to its underside, the bowl has a temperature controlled heater 11 in the form of a PTC (positive temperature coefficient) heater. An ON/OFF switch 12 is mounted in the wall of the housing, as is a therapeutically coloured light 13.

In use a disposable packet 20 of volatilisable-substance matter—an aroma packet—is mounted on the upper ledge, with the base of the dome locking on its card rim 21, the dome and the housing being provided with a non-shown twist lock. The packet has a upper and lower cellulose tissue webs 22,23. These are adhered to the rim by odourless adhesive, with dried vegetable matter 24 captivated between them. Typically dried lavender blooms may be used. The rim is sized to fit the ledge 5. When the aroma of lavender is to be diffused, the bowl is filled until it contains water to a mark 14 and the diffuser is switched on. The water is boiled, causing water vapour to heat the lavender. The lavender's volatile substances are thus diffused via the perforations 15 in the dome into the room where the diffuser has been set up. Any condensate on the dome runs down inside it, past the rim of the packet and returns to the bowl. Typically the water will last for two hours, by which time all the aroma will have been volatised.

As discussed previously, the liquid container, such as the bowl 6, may be fitted with a lid 16 having a water vapor outlet 17. In this embodiment, the liquid is contained in the bowl 6 resting upon the lower ledge 4, and likewise the volatilisable substance 20 is contained in a perforate member (e.g. tissue webs 22,23 or a grid or grill) supported by a support such as the upper ledge 5. The diffuser may include a small container 18 such as a dish holding oil for volatilisation, to provide the option of volatilising the oil instead of the volatilisable substance 20.

Figure 2:
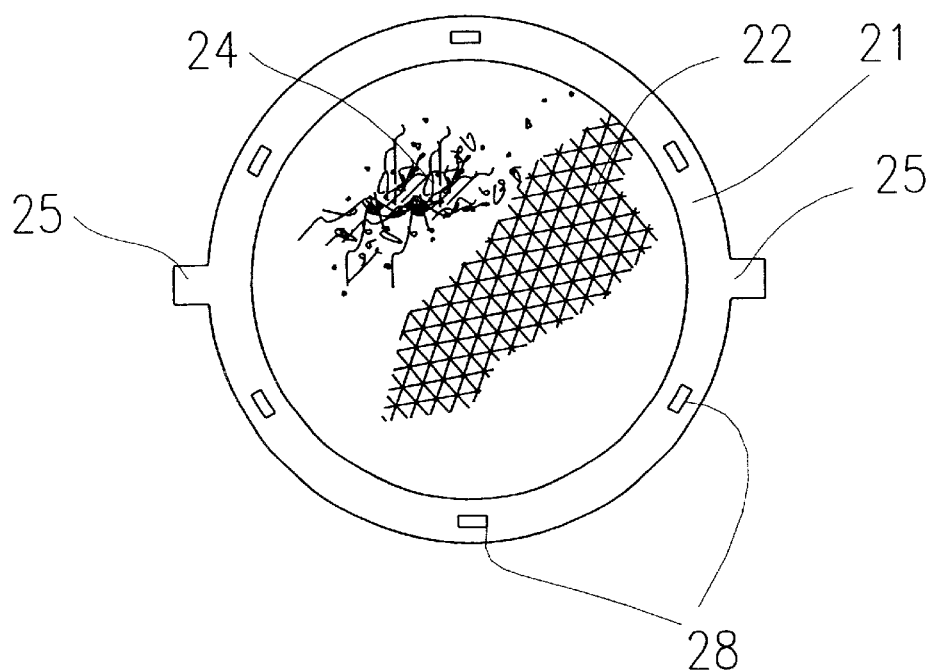
FIG. 2 is a top view of the packet.

To ease fitting and removal of the packet, it is provided on the rim 21 with a pair of diametrically opposed lugs 25, which fit into cut-outs 26 in an up-stand 27 from the ledge 5. The up-stand serves to locate the dome 9. To encourage use of volatilisable material packets which are recommended, they and the rim 5 are preferably provided with complementary formations such as slots 28 in the rim 21 and spigots 29 on the ledge 5. It should be noted that whilst FIG. 2 shows an envisaged arrangement of the lugs and slots around the packet's rim, FIG. 1 illustratively shows on opposite sides a cut-out 26 and a spigot 29, which would not be positioned diametrically opposite each other when the aroma packet is made as shown in of FIG. 2.

The invention is not intended to be restricted to the details of the above described embodiment. For instance a wide variety of aromatic material may be used in the diffuser packet. The packet itself may be of synthetic material. Therapeutic as well as scented materials may be packed. A measuring cup for water to be placed in the bowl can be housed within the dome between uses. Alternatively, a cover can be provide for covering the dome between uses. Where the aromatic material is expected to be released over a longer period than the heater would take to evaporate the amount of water in the container, a controller for intermittently switching the heater on and off may be provided, whereby the water can be made to last longer before it is all evaporated.

What is claimed is:

1. A diffuser comprising:

a housing;

a liquid container in the housing;

a heater for the liquid container, adapted to heat the container sufficiently to vaporise liquid in the container, wherein the heater is controlled by the temperature of the container;

a support for holding volatilisable-substance matter above the liquid container; and a perforate cover over the support, wherein the perforate cover is situated with respect to the volatilisable-substance so that substantially all liquid condensate on the perforate cover can flow past the volatilisable-substance to the liquid container, wherein the liquid container is sufficiently small so that all of the liquid which will be put in the container is located directly below the volatilisable-substance matter, and wherein the perforate cover is sufficiently large so that all of the volatilisable matter will be directly below the perforate cover.

2. A diffuser as claimed in claim 1, wherein the liquid container is substantially closed, with a water vapour outlet.

3. A diffuser as claimed in claim 1, wherein the liquid container is open within the housing.

4. A diffuser as claimed in claim 1, wherein the support is integral with the liquid container.

5. A diffuser as claimed in claim 1, wherein the support is provided on an extension of the housing above the container.

6. A diffuser as claimed in claim 1, further including a perforate member for holding the volatilisable-substance matter.

7. A diffuser as claimed in claim 1, further including an absorbent pad for use with extract in the form of an essential oil.

8. A diffuser as claimed in claim 1, further including a small container for holding essential oil for volatilisation.

9. A diffuser as claimed in claim 1, further including a perforate cover over the support.

10. A disposable packet of volatilisable-substance matter for use with a diffuser as claimed in claim 1, the packet comprising:

a porous envelope, which is at once sufficiently porous to allow passage of steam and sufficiently strong to retain its integrity in steam;

a rim adapted to fit a support of the diffuser; and a quantity of volatilisable-substance matter enclosed within the porous envelope, wherein the rim includes rim formations which complement formations of the diffuser and which facilitate attachment of the rim to the support.

11. A disposable packet of volatilisable-substance matter as claimed in claim 10, wherein the envelope comprises an upper web and a lower web, each of tissue and each attached to the rim.

12. A disposable packet of volatilisable-substance matter as claimed in claim 11, wherein the webs and the rim are of cellulose material.

13. The disposable packet of claim 10, wherein the rim formations include at least one slot and at least one lug.

14. The disposable packet of claim 10, wherein the packet is circular and biconvex, and is for holding a dried organic material.

* * * * *